United States Patent
Kim et al.

(10) Patent No.: US 9,029,591 B2
(45) Date of Patent: May 12, 2015

(54) GEM-DINITRO ESTER COMPOUND AS ENERGETIC MATERIAL AND PREPARATION METHOD THEREOF

(71) Applicant: Agency for Defense Development, Daejeon (KR)

(72) Inventors: Seung-Hee Kim, Daejeon (KR); Jin-Seuk Kim, Daejeon (KR)

(73) Assignee: Agency for Defense Development, Daejeon (KR)

( * ) Notice: Subject to any disclaimer, the term of this patent is extended or adjusted under 35 U.S.C. 154(b) by 22 days.

(21) Appl. No.: 13/869,875

(22) Filed: Apr. 24, 2013

(65) Prior Publication Data

US 2014/0121401 A1     May 1, 2014

(30) Foreign Application Priority Data

Oct. 30, 2012   (KR) .................... 10-2012-0121335

(51) Int. Cl.
    *C07C 205/00*  (2006.01)
    *C07C 205/51*  (2006.01)
(52) U.S. Cl.
    CPC .................... *C07C 205/51* (2013.01)
(58) Field of Classification Search
    CPC .................................................... C07C 205/51
    USPC ....................................................... 560/156
    See application file for complete search history.

(56) References Cited

U.S. PATENT DOCUMENTS 5,061,330 A    10/1991  Reed, Jr. et al.

FOREIGN PATENT DOCUMENTS

KR    10-2003-0087341 A    11/2003

OTHER PUBLICATIONS

Shechter et al., "The Condensation of 1,1-Dintroethane with Electronegativity Substituted Unsaturated Compounds. The Synthesis of 3,3-Dinitro-1-butene," J. Am. Chem. Soc., 73, 1276-1278, 1951.*
Veldurthy et al., "Magnesium—Lanthanum Mixed Metal Oxide: a Strong Solid Base for the Michael Addition Reaction," Adv. Synth. Catal., 347, 767-771, 2005.*
George Wypych, "Handbook of Plasticizers," ChemTec Publishing, 2004.

* cited by examiner

*Primary Examiner* — Paul A Zucker
*Assistant Examiner* — Mark Luderer
(74) *Attorney, Agent, or Firm* — LRK Patent Law Firm

(57) ABSTRACT

Provided is a gem-dinitro ester compound, represented by Formula 1 below:

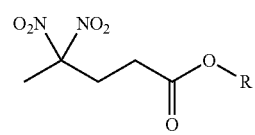

[Formula 1]

wherein R is a substituted or unsubstituted straight-chain or side-chain alkyl group of $C_2$–$C_{12}$.

2 Claims, No Drawings

GEM-DINITRO ESTER COMPOUND AS ENERGETIC MATERIAL AND PREPARATION METHOD THEREOF

CROSS REFERENCE TO RELATED APPLICATION

This application claims the benefit of Korean Patent Application No. 10-2012-0121335, filed on Oct. 30, 2012, which is hereby incorporated by reference in its entirety into this application.

BACKGROUND OF THE INVENTION

1. Technical Field

The present invention relates to gem-dinitro ester compounds as energetic materials and a method of preparing the same.

2. Description of the Related Art

A composite explosive has been developed in order to improve both performance and insensitivity of an explosive. Generally, a composite explosive includes a granular molecular explosive, such as a research development explosive (RDX), to provide explosiveness, and a binder composition. The binder composition is used in an amount of 2~20 wt % based on the total amount of the composite explosive, and functions to provide dimensional stability and obtuseness to the granular molecular explosive. However, the binder composition does not have a nitro group for exhibiting explosiveness, thus deteriorating the total explosiveness thereof.

The binder composition includes a polymer and a plasticizer. In the binder composition, the content of a polymer is about three times compared to that of a plasticizer, so the characteristics of a plasticizer are very important.

In order to maximize the performance of a composite explosive, research into introducing a nitro group into a plasticizer has been widely carried out. Like this, the plasticizer, into which a nitro group is introduced, is referred to as an energetic plasticizer. Research into the energetic binder has also been widely carried out. However, typical plasticizers actually applied to explosives are formal-based or acetal-based plasticizers such as bis(2,2-dinitropropyl) formal (represented by Formula A below) or bis(2,2-dinitropropyl)acetal (represented by Formula B below).

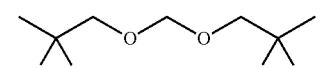

[Formula A]

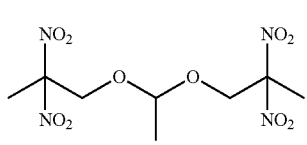

[Formula B]

A mixing process is needed in order to prepare a composite explosive. Generally, the mixing process is carried out at 60° C. in order to decrease the viscosity of a polymer. The molecular explosive, such as RDX, used in the composite explosive is recrystallized, and then its shape is adjusted into a polygon. However, when the shape-adjusted molecular explosive is mixed with the energized plasticizer and then the mixture is cooled to room temperature, the shape-adjusted molecular explosive is dissolved in the energetic plasticizer and then crystallized again. In this process, the molecular explosive is crystallized in various undefined shapes, such as a needle and the like, not a polygon. As such, when the shape-changed molecular explosive is included in the composite explosive, the sensitivity of the composite explosive is increased.

The sensitivity of the composite explosive attributable to the plasticizer is changed by the chemical structure of the plasticizer. That is the difference in structure between DOA and the energized plasticizer is determined according to whether or not a plasticizer includes a nitro group as an energy group. When a nitro group is introduced into a plasticizer, a molecular explosive, which is a solid filler, is dissolved in the plasticizer due to the strong polarity of the nitro group in the mixing process at 60° C., and when temperature is lowered, the molecular explosive is precipitated into a solid. During this precipitation process, the shape of the molecular explosive is changed into a sensitive shape, so that the shape-changed molecular explosive makes the composite explosive sensitive.

SUMMARY OF THE INVENTION

Accordingly, the present invention has been devised to solve the above-mentioned problems. The present inventors found that the sensitivity of a composite explosive results from excessively introducing a nitro group into an energetic plasticizer in order to increase energy density. That is, when a nitro group is excessively introduced, it is advantageous in terms of energy density, but is problematic in that the viscosity and polarity of the plasticizer are increased due to the excessive amount of the nitro group added to allow a molecular explosive to be dissolved in the plasticizer, thus causing the shape of the molecular explosive to change.

Therefore, an object of the present invention is to provide a gem-dinitro ester compound, which is a plasticizer having a chemical structure that can increase the energy density of a composite explosive and minimize the side effect of dissolving a molecular explosive, and a method of preparing the same.

In order to accomplish the above object, an aspect of the present invention provides a gem-dinitro ester compound, represented by Formula 1 below:

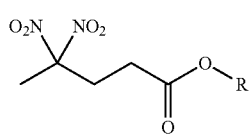

[Formula 1]

wherein R is a substituted or unsubstituted straight-chain or side-chain alkyl group of $C_2$~$C_{12}$.

Another aspect of the present invention provides a method of preparing a gem-dinitro ester compound represented by Formula 1 below by reacting a compound represented by Formula 2 with a compound represented by Formula 3:

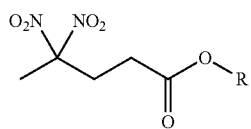

[Formula 1]

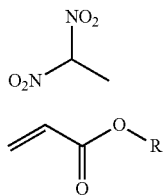
[Formula 2]

[Formula 3]

wherein R is a substituted or unsubstituted straight-chain or side-chain alkyl group of $C_2$~$C_{12}$.

Still another aspect of the present invention provides a composite explosive including the gem-dinitro ester compound.

DESCRIPTION OF THE PREFERRED EMBODIMENTS

Hereinafter, preferred embodiments of the present invention will be described in detail with reference to the attached drawings.

The present invention provides a gem-dinitro ester compound, represented by Formula 1 below:

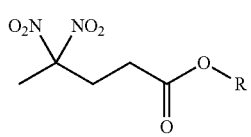
[Formula 1]

wherein R is a substituted or unsubstituted straight-chain or side-chain alkyl group of $C_2$~$C_{12}$.

The substituted or unsubstituted straight-chain or side-chain alkyl group of $C_2$~$C_{12}$ may be a substituted or unsubstituted straight-chain or side-chain butyl group, pentyl group, hexyl group, heptyl group or octyl group.

The octyl group may include an octane-3-yl group.

The gem-dinitro ester compound can be usefully used as a plasticizer for manufacturing a composite explosive.

In the gem-dinitro ester compound of the present invention, a gem-dinitro group, as an energy group, is introduced into a side thereof, and a straight-chain or side-chain alkyl group, which is a nonpolar compound, is introduced into a side opposite to the side thereof, so that the polarity of the gem-dinitro ester compound (as an energetic plasticizer) is lowered to prevent the shape of a molecular explosive front being changed during a process of manufacturing a composite explosive, thereby lowering the impact sensitivity of the composite explosive.

Further, the present invention provides a method of preparing a gem-dinitro ester compound represented by Formula 1 below by reacting a compound represented by Formula 2 with a compound represented by Formula 3:

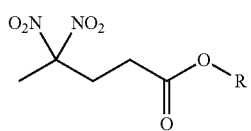
[Formula 1]

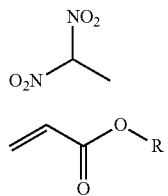
[Formula 2]

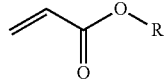
[Formula 3]

wherein R is a substituted or unsubstituted straight-chain or side-chain alkyl group of $C_2$~$C_{12}$.

The substituted or unsubstituted straight-chain or side-chain alkyl group of $C_2$~$C_{12}$ may be a substituted or unsubstituted straight-chain or side-chain butyl group, pentyl group, hexyl group, heptyl group or octyl group.

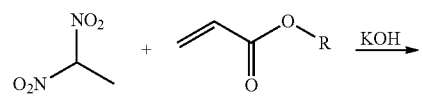
[Reaction Formula 1]

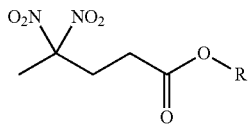

As shown in Reaction Formula 1 above, the reaction of the compound represented by Formula 2 with the compound represented by Formula 3 may be performed in the presence of a strong base. Potassium hydroxide (KOH) or the like may be used as the strong base.

The reaction of the compound represented by Formula 2 with the compound represented by Formula 3 may be performed using at least one solvent selected from the group consisting of lower alcohols of $C_1$~$C_4$ and water.

Methanol or the like may be used as the lower alcohol of $C_1$~$C_4$.

According to the method of the present invention, the gem-dinitro ester compound can be obtained in a high yield by the one-step synthesis of Michael addition reaction using 1,2-dinitroethane (commercially available raw material) and an acrylic compound.

Further, the present invention provides a composite explosive including the gem-dinitro ester compound.

The composite explosive of the present invention exhibits excellent explosiveness, and has excellent insensitivity to impact.

Hereinafter, the present invention will be described in more detail with reference to the following Examples. However, these Examples are set forth to illustrate the present invention, and the present invention is not limited thereto and may be variously modified. The scope of the present invention will be defined by technical ideas of the accompanying claims.

Example 1

Synthesis of Butyl 4,4-dinitropentanoate

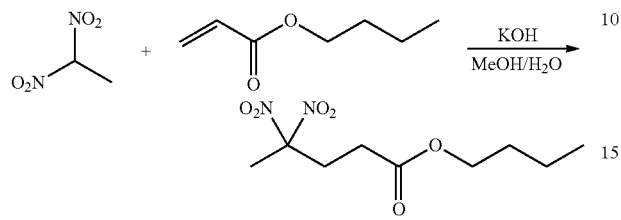

Dinitroethane (12 g, 0.10 mol) and potassium hydroxide (6 g, 0.11 mol) were dissolved in 100 mL of water to form a first solution. 500 mL of water was added to the first solution to dissolve a salt remaining in the first solution to form a second solution. Butyl acrylate (36 mL, 0.25 mol) was mixed with 300 mL of methanol, and then the mixture was slowly added to the second solution to form a third solution. The third solution was stirred at room temperature for 3 hours. The reaction product was extracted by diethyl ether, and was then distilled under reduced pressure to obtain yellow liquid butyl 4,4-dinitropentanoate (21.5 g, yield: 87%).

Results of NMR and thermoanalysis:
$^1$H NMR (CDCl$_3$) δ 4.12 (t, 2H), 2.87 (t, 2H), 2.48 (t, 2H), 2.15 (s, 3H), 1.63 (m, 2H), 1.40 (m, 2H), 0.95 (t, 3H)
IR (neat) v$_{max}$: 2962, 2875, 1733, 1562, 1325, 1188, 1109, 847 cm$^{-1}$
Tg (glass transition temperature): −96.07° C.

Example 2

Synthesis of Pentyl 4,4-dinitropentanoate

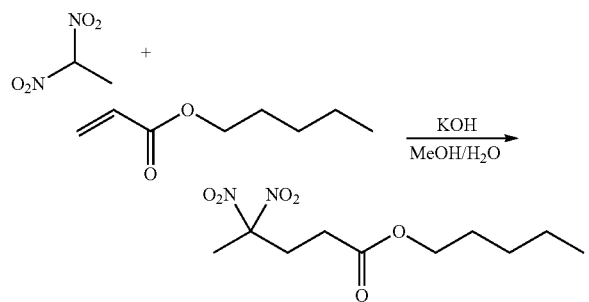

Dinitroethane (2.4 g, 0.02 mol) and potassium hydroxide (1.2 g, 0.022 mol) were dissolved in 50 mL of water to form a first solution. 50 mL of water was added to the first solution to dissolve a salt remaining in the first solution to form a second solution. Pentyl acrylate (8 mL, 0.05 mol) was mixed with 50 mL of methanol, and then the mixture was slowly added to the second solution to form a third solution. The third solution was stirred at room temperature for 3 hours. The reaction product was extracted by diethyl ether, and was then distilled under reduced pressure to obtain yellow liquid pentyl 4,4-dintitropentanoate (4.3 g, yield: 82%).

Results of NMR and Thermoanalysis:
$^1$H NMR (CDCl$_3$) δ 4.13 (t, 2H), 2.85 (t, 2H), 2.35 (t, 2H), 2.23 (s, 3H), 1.63 (m, 2H), 1.39 (m, 2H), 1.32 (m, 2H), 0.95 (t, 3H)
IR (neat) v$_{max}$: 2944, 2850, 1722, 1580, 1195, 1135, 856 cm$^{-1}$
Tg (glass transition temperature): −95.65° C.

Example 3

Synthesis of Hexyl 4,4-dinitropentanoate

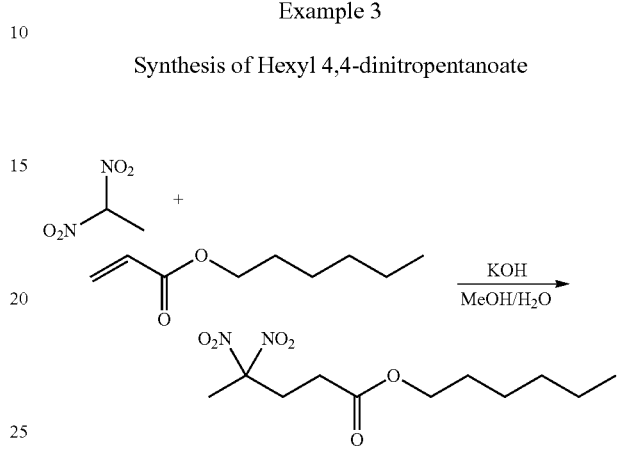

Dinitroethane (2.4 g, 0.02 mol) and potassium hydroxide (1.2 g, 0.022 mol) were dissolved in 50 mL of water to form a first solution. 50 mL of water was added to the first solution to dissolve a salt remaining in the first solution to form a second solution. Hexyl acrylate (8.8 mL, 0.05 mol) was mixed with 50 mL of methanol, and then the mixture was slowly added to the second solution to form a third solution. The third solution was stirred at room temperature for 4 hours. The reaction product was extracted by diethyl ether, and was then distilled under reduced pressure to obtain yellow liquid hexyl 4,4-dinitropentanoate (4.5 g, yield: 81%).

Results of NMR and Thermoanalysis:
$^1$H NMR (CDCl$_3$) δ 4.10 (t, 2H), 2.85 (t, 2H), 2.45 (t, 2H), 2.13 (s, 3H), 1.62 (m, 2H), 1.34 (m, 6H), 0.90 (t, 3H)
IR (neat) v$_{max}$: 2931, 2861, 1734, 1564, 1187, 1109, 847 cm$^{-1}$
Tg (glass transition temperature): −94.28° C.

Example 4

Synthesis of Heptyl 4,4-dinitropentanoate

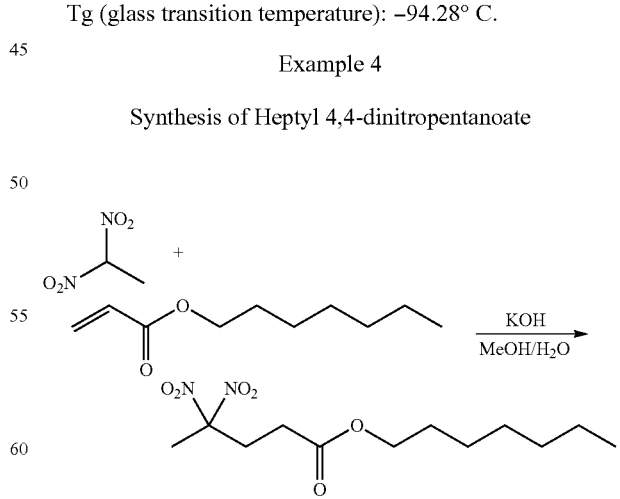

Dinitroethane (2.4 g, 0.02 mol) and potassium hydroxide (1.2 g, 0.22 mol) were dissolved in 50 mL of water to form a first solution. 50 mL of water was added to the first solution to dissolve a salt remaining in the first solution to form a second solution. Heptyl acrylate (9.5 mL, 0.05 mol) was mixed with 50 mL of methanol, and then the mixture was slowly added to the second solution to form a third solution. The third solution was stirred at room temperature for 3 hours. The reaction product was extracted by diethyl ether, and was then distilled under reduced pressure to obtain yellow liquid heptyl 4,4-dinitropentanoate (4.8 g, yield: 83%).

Results of NMR and Thermoanalysis:
$^1$N NMR (CDCl$_3$) δ 4.11 (t 2H), 2.86 (t, 2H), 2.45 (t, 2H), 2.13 (s, 3H), 1.63 (m, 2H), 1.30 (m, 8H), 0.90 (t, 3H)
IR (neat) v$_{max}$: 2956, 2929, 2858, 1734, 1564, 1186, 1109, 847 cm$^{-1}$
Tg (glass transition temperature): −94.84° C.

Example 5

Synthesis of Octyl 4,4-dinitropentanoate

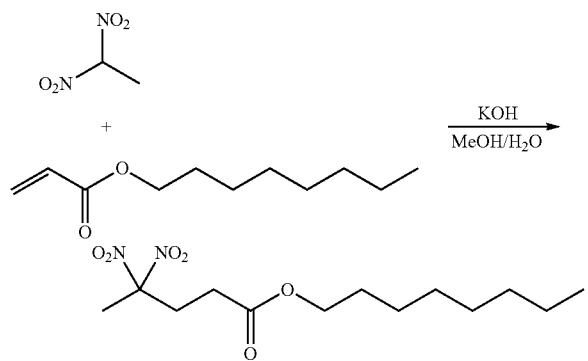

Dinitroethane (2.4 g, 0.02 mol) and potassium hydroxide (1.2 g, 0.22 mol) were dissolved in 50 mL of water to form a first solution. 50 mL of water was added to the first solution to dissolve a salt remaining in the first solution to form a second solution. Octyl acrylate (10.2 mL, 0.05 mol) was mixed with 50 mL of methanol, and then the mixture was slowly added to the second solution to form a third solution. The third solution was stirred at room temperature for 4 hours. The reaction product was extracted by diethyl ether, and was then distilled under reduced pressure to obtain yellow liquid octyl 4,4-dinitropentanoate (5.0 g, yield: 82%).

Results of NMR and Thermoanalysis:
$^1$H NMR (CDCl$_3$) δ 4.12 (t, 2H), 2.84 (t, 2H), 2.36 (t, 2H), 2.21 (s, 3H), 1.63 (m, 2H), 1.35 (m, 10H), 0.88 (t, 3H)
IR (neat) v$_{max}$: 2987, 2896, 1720, 1578, 1355, 1173, 1131, 869 cm$^{-1}$
Tg (glass transition temperature): −92.35° C.

Example 6

Synthesis of Octane-3-yl 4,4-dinitropentanoate

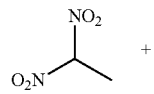

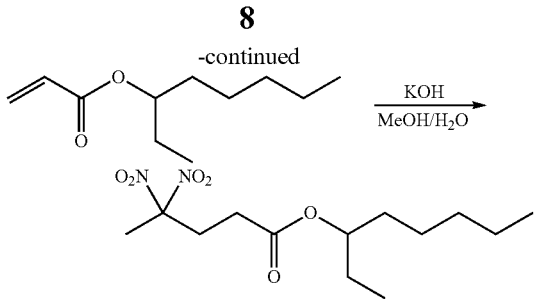

Dinitroethane (2.4 g, 0.02 mol) and potassium hydroxide (1.2 g, 0.22 mol) were dissolved in 50 mL of water to form a first solution. 50 mL of water was added to the first solution to dissolve a salt remaining in the first solution to form a second solution. Octane-3-yl acrylate (8.3 mL, 0.05 mol) was mixed with 50 mL of methanol, and then the mixture was slowly added to the second solution to form a third solution. The third solution was stirred at room temperature for 5 hours. The reaction product was extracted by diethyl ether, and was then distilled under reduced pressure to obtain yellow liquid octane-3-yl 4,4-dinitropentanoate (4.9 g, yield: 80%).

Results of NMR and Thermoanalysis:
$^1$H NMR (CDCl$_3$) δ 4.04 (dd, 2H), 2.86 (t, 2H), 2.46 (t, 2H), 2.14 (s, 3H), 1.55 (m, 1H), 1.31 (m, 8H), 0.89 (t, 3H)
IR (neat) v$_{max}$: 2960, 2930, 2872, 1734, 1564, 1394, 1187, 847 cm$^{-1}$
Tg (glass transition temperature): −90.65° C.

As described above, the gem-dinitro ester compound of the present invention is used as a plasticizer, and serves to increase the energy density of a composite explosive and minimize the side effect of dissolving a molecular explosive.

Therefore, the gem-dinitro ester compound can improve the explosiveness of a composite explosive and can improve the insensitivity of the composite explosive to impact.

Further, according to the method of the present invention, the gem-dinitro ester compound can be obtained in a high yield by the one-step synthesis of Michael addition reaction using 1,2-dinitroethane (commercially available raw material) and an acrylic compound.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A gem-dinitro ester compound, represented by Formula 1 below:

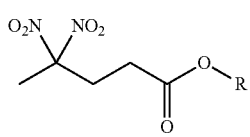

[Formula 1]

wherein R is a substituted or unsubstituted straight-chain or side-chain alkyl group of C$_7$ to C$_{12}$.

2. The gem-dinitro ester compound of claim 1, wherein the substituted or unsubstituted straight-chain or side-chain alkyl group of C$_7$ to C$_{12}$ is a substituted or unsubstituted straight-chain or side-chain heptyl group or octyl group.

* * * * *